United States Patent [19]

Begemann

[11] Patent Number: 5,470,344
[45] Date of Patent: Nov. 28, 1995

[54] RATE RESPONSIVE PACEMAKE WITH IMPROVED RATE CHANGE DYNAMICS AND PACING METHOD

[75] Inventor: Malcolm J. S. Begemann, Velp, Netherlands

[73] Assignee: Vitatron Medical, B.V., Dieren, Netherlands

[21] Appl. No.: 132,758

[22] Filed: Oct. 6, 1993

[51] Int. Cl.⁶ .................................................. A61N 1/365
[52] U.S. Cl. ........................................................ 607/17
[58] Field of Search ........................................ 607/17–26

[56] References Cited

U.S. PATENT DOCUMENTS

| | | | |
|---|---|---|---|
| 4,091,726 | 2/1990 | Hansen | 607/17 |
| 4,485,813 | 12/1984 | Anderson et al. | 128/675 |
| 4,688,573 | 8/1987 | Alt | 128/419 PG |
| 4,782,836 | 11/1988 | Alt | 128/419 PG |
| 5,052,388 | 10/1991 | Sivula et al. | 128/419 PG |
| 5,063,927 | 11/1991 | Webb et al. | 607/18 |
| 5,065,759 | 11/1991 | Begemann et al. | 128/419.0 |
| 5,134,997 | 8/1992 | Bennett et al. | 607/17 |
| 5,304,208 | 4/1994 | Inguaggiato et al. | 607/17 |
| 5,312,453 | 5/1994 | Shelton et al. | 607/19 |

FOREIGN PATENT DOCUMENTS

9216258 10/1992 WIPO ........................................ 607/9

Primary Examiner—William E. Kamm
Assistant Examiner—Marianne Parker
Attorney, Agent, or Firm—Woodcock, Washburn, Kurtz, Mackiewicz & Norris

[57] ABSTRACT

A rate responsive pacemaker and method of pacing, having circuitry for controlling the rate of change of pacing rate in response to varying rate sensor signals. The pacemaker increments or decrements pacing rate each cycle, the change in rate being limited as a function of pacing rate, rate of change of sensor rate; the magnitude of the difference between sensor rate and pacing rate; whether prior cycles ended in sense or pace events; and/or a separate fast response sensor.

11 Claims, 5 Drawing Sheets

RATE RESPONSIVE PACEMAKE WITH IMPROVED RATE CHANGE DYNAMICS AND PACING METHOD

BACKGROUND OF THE INVENTION

1. Field of the Invention

The present invention relates to cardiac pacers, and more particularly, to a rate responsive cardiac pacer which automatically controls the speed with which pacing rate can be changed so as to provide a more physiological response to changing cardiac demand.

2. Description of the Prior Art

The rate responsive cardiac pacemaker is now acknowledged to provide a significant improvement over prior fixed-rate cardiac pacemakers. Indeed, rate response techniques have been applied to both single and dual chamber pacemakers, and are able to control pacing rate as a function of one or more measured parameters which are directly or indirectly related to cardiac demand. Such measured parameters include, for example, the physical activity or movement of the patient, right ventricular blood pressure and change of such blood pressure over time, venous blood temperature, venous blood oxygen saturation, respiration, minute ventilation and Q-T interval. A more recent advent is the employment of two or more sensors and the use of algorithms for obtaining an optimized sensor-heart rate correlation function. See, for example, U.S. Pat. No. 5,065,759, entitled "Pacemaker With Optimized Rate Responsiveness and Method of Rate Control," assigned to the same assignee as this application, and incorporated herein by reference. An advantage of the combined sensor approach is to provide a sensor response which accurately tracks cardiac demand both during fast time period episodes and during more stable steady state patient conditions. For example, the Q-T parameter is very reliable as a steady state indicator of metabolic demand, but does not respond quickly to fast changes, such as at the onset of exercise. On the other hand, the activity-type sensor, such as described in U.S. Pat. No. 4,485,813, issued to Anderson et al., and assigned to Medtronic, Inc., provides a faster response to changing patient conditions, even though it may not be as accurate an indicator of quiescent demand.

A problem that pacemaker designers have encountered, but not yet resolved fully satisfactorily, is that of translating sensor indications of desired pacing rate into actual changes in pacing rate. By way of example, at both the onset and termination of exercise the body's physiological response is known to be different from what accurate sensor signals would otherwise indicate. Thus, at the onset of exercise, the heart does not increase rate as a step function, but increases over a period of time and as a function of the degree of exercise. Likewise, following termination of exercise, the physiological heart rate decays in accordance with a certain decay function. Accordingly, there have been efforts to resolve the discrepancy between normal heart deceleration function at the end of physiological stresses such as physical activity, and the normal physiological decay function. See, for example, U.S. application Ser. No. 07/567,204, filed Aug. 14, 1990, Bennett et al., entitled "Rate Responsive Pacemaker and Pacing Method"; and U.S. patent application Ser. No. 880,877, filed May 11, 1992, "Work-Modulated Pacing Rate Deceleration," both assigned to Medtronic, Inc.

The inventor of this invention has also observed that the appropriate response of a pacemaker to changed sensor indication of heart rate is generally a function of patient history, and specifically recent heart rate (paced or natural). This is a general rule, and is the case not just at transitions from rest to exercise or exercise to rest. Thus, if a patient has already had a relatively high heart rate, e.g., 85 bpm, and the sensor indication calls for a still increased heart rate, the correct physiological response may be different from the situation where the patient starts with a lower heart rate, e.g., around 70 bpm.

As a consequence of the above observations, it is seen that there is a need for an improved pacemaker apparatus, and method of controlling the rate responsiveness of a pacemaker, for providing a more appropriately physiological response under conditions where accurate sensor information concerning cardiac demand is available.

SUMMARY OF THE INVENTION

It is an object of this invention to provide a rate responsive pacemaker with improved rate change dynamics whereby changes in pacing rate, both rise and decay, follow an improved and more physiological pattern.

In accordance with the present invention, there is provided a pacemaker and a method of controlling the rate thereof, wherein the sensor rate information is analyzed continuously and wherein the rise time for increasing rates and the decay time for decreasing rates are adjusted as a function of patient history such as initial rate, the difference between the sensor indicated rate and present natural rate, and the rate of change of the sensor indicated rate. Preferably on a cycle-by-cycle basis the pacemaker determines an indicated sensor rate (R), the difference between the sensor rate and the then current pacing rate (R-r), and calculates a measure of the time rate of change of R. The pacemaker then determines whether rate should be incremented or decremented (or left unchanged). A first value or change in r ($\Delta r$) is obtained as a function of current pacing rate. The measure of time rate of change in R is then compared to a rise threshold figure or a decay threshold figure, depending upon whether a rise or decay in pacing rate is indicated. If the time rate of change in R exceeds the corresponding threshold, a further adjustment to $\Delta r$ is made, following which pacing rate is increased or decreased by the adjusted $\Delta r$.

The control of the per cycle change in pacing rate as set forth above, is suitably carried out with the aid of a programmed microprocessor and associated memory. The algorithm for carrying out the novel functions of this invention may be supplemented to modify decay time as a function of total patient work during exercise, in accordance with the aforementioned U.S. application Ser. No. 880,877, which is incorporated herein by reference.

DESCRIPTION OF THE PREFERRED EMBODIMENT

Figure 1A:
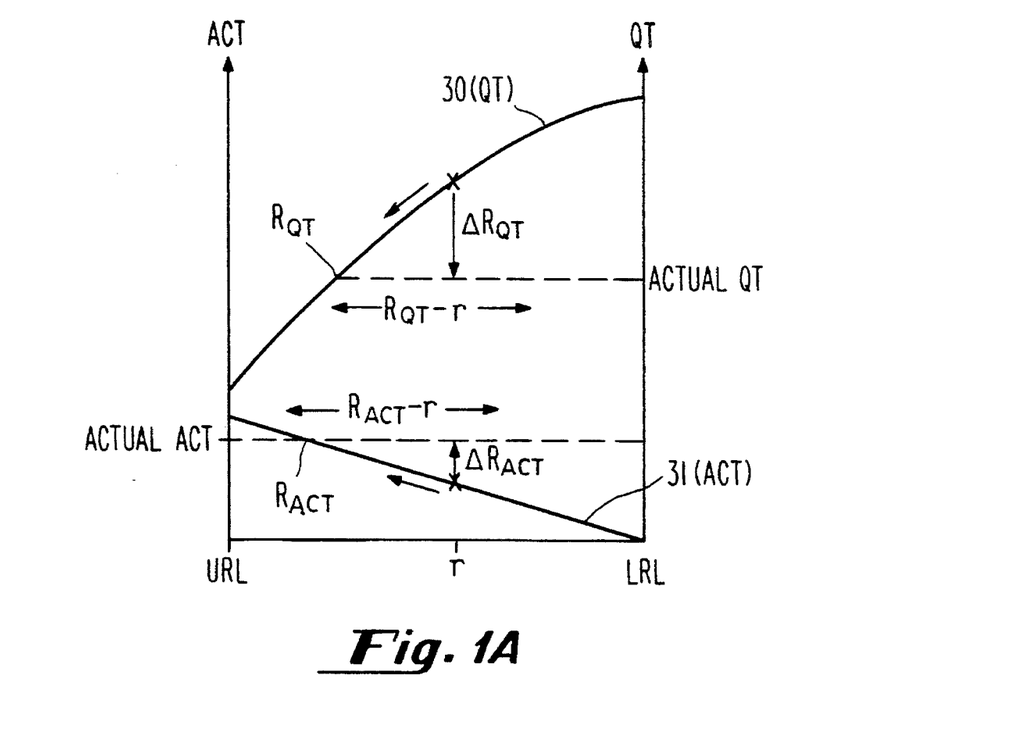
FIG. 1A presents curves showing correlation of Q-T interval with pacing rate, and a measure of activity (ACT) with pacing rate.
Figure 1B:
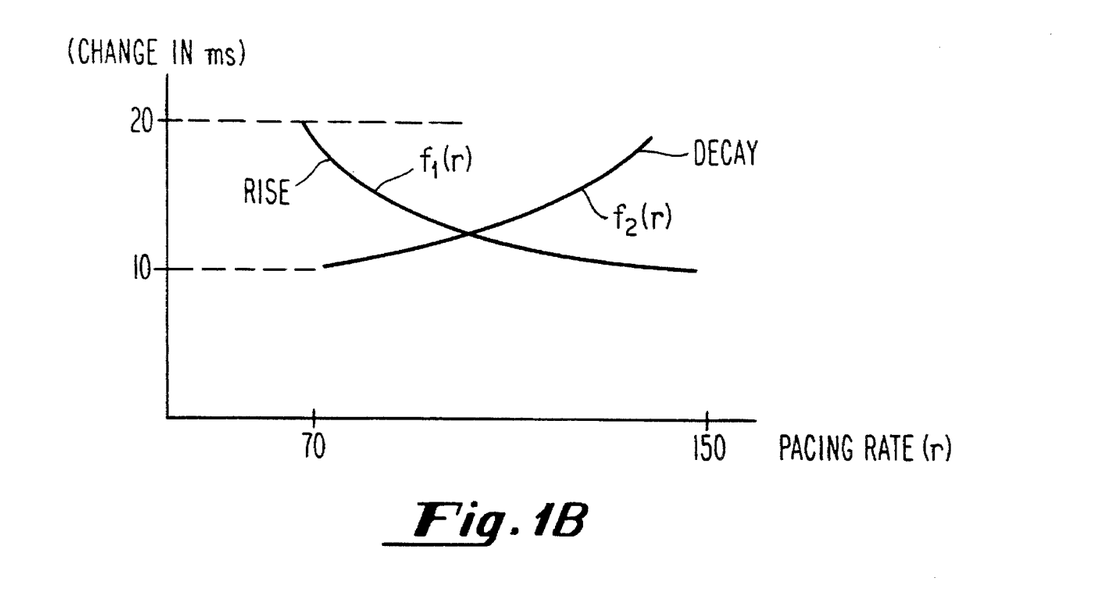
FIG. 1B is an graph indicating pacing rate increment versus pacing rate, for both rise and decay situations.

Referring now to FIGS. 1A and 1B, there are shown curves which illustrate the problems to be solved by this invention. As seen in FIG. 1A, there are shown two curves correlating pacing rate (r) with a sensed parameter. Thus, a first curve 30 correlates Q-T interval with pacing rate, and a second curve correlates activity (ACT) with pacing rate. These curves are given for illustrative purposes only, and it is understood that the precise correlation curve between the sensed parameter and pacing rate may be adjusted for any given patient. Reference is made to U.S. Pat. No. 5,065,759, entitled "Pacemaker With Optimized Rate Responsiveness and Method of Rate Control," which is incorporated herein by reference, and which discloses an arrangement for utilizing two parameters to obtain an indication of desired pacing rate. As used in this invention, reference to the sensor signal, or indicated sensor rate (R), may refer to either one or plural sensors.

The situation where there has been a sharp increase in exercise level of the patient is illustrated. Prior to the increase in exercise, it is assumed that pacing rate corresponded to the point "X" on each of the curves. Following the increase in exercise, each sensor calls for a higher R, and thus a shorter pacing interval. The activity sensor is a relatively fast response time sensor, indicating an elevated target pacing rate as shown at $R_{ACT}$, corresponding to "ACTUAL ACT." The Q-T interval indicates a pacing rate as shown at $R_{QT}$, corresponding to "ACTUAL QT." For either sensor, the change from r to R could constitute a large (and unacceptable) jump. In practice, the pacemaker does not jump directly to the target pacing rate, i.e., immediately switch to a pacing rate R. Rather, the pacemaker may suitably increase rate by an increment $\Delta r$ which establishes a limit on the rise time of the pacing rate. Likewise, at the cessation of exercise, where R may call for a sharp drop in pacing rate, the pacemaker imposes a decay time which limits the speed with which pacing rate is decreased down toward a normal base rate. See, for example, the discussion in above-referenced Ser. No. 880,877.

As discussed above, it is my observation that the rise time or decay time for use in a pacemaker is properly a function of the pacing rate, and should not be a constant value. Thus, the permitted rise time may vary from a maximum at a relatively low rate to a minimum level at a relatively high rate. As illustrated in FIG. 1B, if a patient's rate has been at about 70 bpm, and the sensor rate R is indicated at a higher rate such as 150 bpm, the initial incremental rise ($\Delta r$) can correspond to an incremental decrease in time interval of, e.g., 20 ms. The value of $\Delta r$ decreases as the pacing rate is driven upward toward the target rate of 150 bpm. Thus, if a patient had started with a rate of about 90 bpm, and then underwent an increase in exercise, the rise time corresponds to a smaller incremental increase in rate, to permit a more physiological step up of pacing rate toward the target rate. Likewise, when a patient has been paced at a relatively high rate (e.g., 150 bpm) and there is termination of exercise, the initial decay rate can be set to decrement pacing rate at a larger interval (e.g., 20 ms), whereas the decay rate is less for a starting point where the pacing rate was closer to 70 bpm.

Figure 2A:
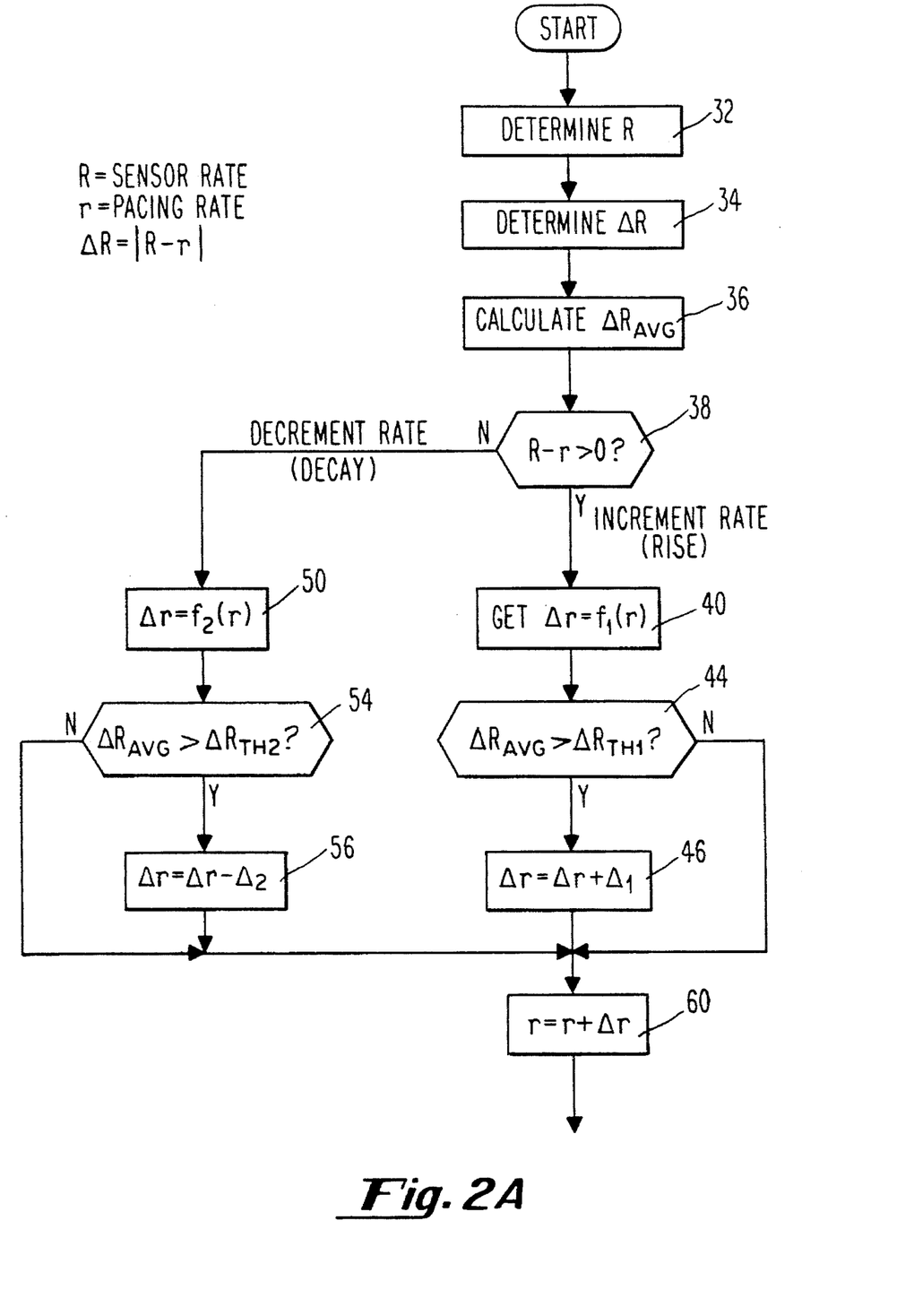
FIGS. 2A and 2B are flow diagrams depicting the operation of a control algorithm in accordance with this invention, for controlling the pacing rate increment as a function of pacing rate and/or time rate of change of the sensor rate.
Figure 3:
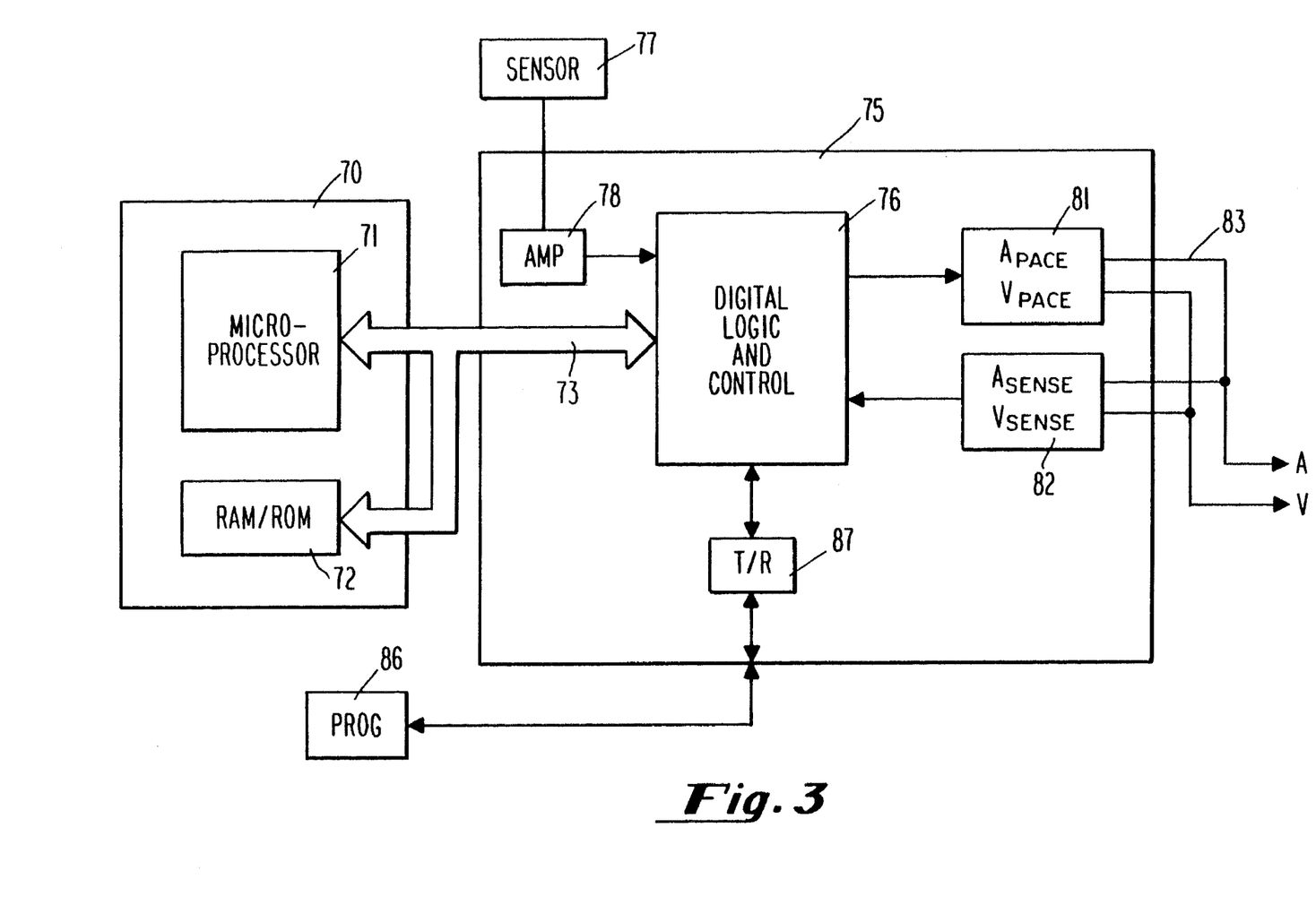
FIG. 3 is a block diagram of the main components of a pacemaker in accordance with this invention.

Referring now to FIG. 2A, there is shown a flow diagram for logic steps to be taken in a pacemaker of this invention. Suitably the steps may be embodied in software such a contained in microprocessor circuitry 70 as illustrated in FIG. 3. However, any equivalent hardware or combination of hardware and software may be utilized for carrying out the steps of determining how to vary the rise time or decay time for a pacemaker of this invention.

At step 32, the indicated pacing rate R is determined from the sensor information. At step 34, the absolute difference $\Delta R$ between R and the present pacing rate (R-r) is determined. If this absolute difference is less than a predetermined minimum amount, $\Delta R$ is set to zero. At step 36, a measure of the time rate of change of the sensor indicated pacing rate is obtained. A calculation of $\Delta R_{AVG}$ is made, which is an average of $\Delta R$ over the last n cycles. Thus, if n is a small number, e.g., 2–4, $\Delta R_{AVG}$ will give an indication of any substantial change in R. Note that also that the change in R-r from the last cycle can also be calculated, and used as a measure of time rate of change of the sensor rate. At step 38, it is determined whether R-r is greater than zero. If yes, meaning that the pacemaker wants to increase rate, the program branches to block 40. At 40, $\Delta r$ is obtained from memory in accordance with the formula $\Delta r = f_1(r)$ shown as the rise curve in FIG. 1B. Following this, the program proceeds to block 44 and determines whether $\Delta R_{AVG}$ is greater than $\Delta R_{TH1}$, a predetermined stored value. This comparison determines whether there has been a substantial change in R, indicating that a further more aggressive change in pacing rate is in order. If no, the program branches to block 60, but if yes, the program branches to block 46 and increments $\Delta r$ by a factor $\Delta_1$. Then at block 60, pacing rate is set equal to r (the prior pacing rate)+$\Delta r$. Going back to block 38, if the answer is no, this means that the pacemaker wants to decrease pacing rate, and select a decay time. At block 50, $\Delta r$ is set equal to $f_2(r)$. The program then goes to block 54 and compares $\Delta R_{AVG}$ to a second stored threshold $\Delta R_{TH2}$. If this comparison is positive, then $\Delta r$ is further decremented by $\Delta_2$ at 56, to decrease pacing rate at a greater decay rate.

Figure 2B:
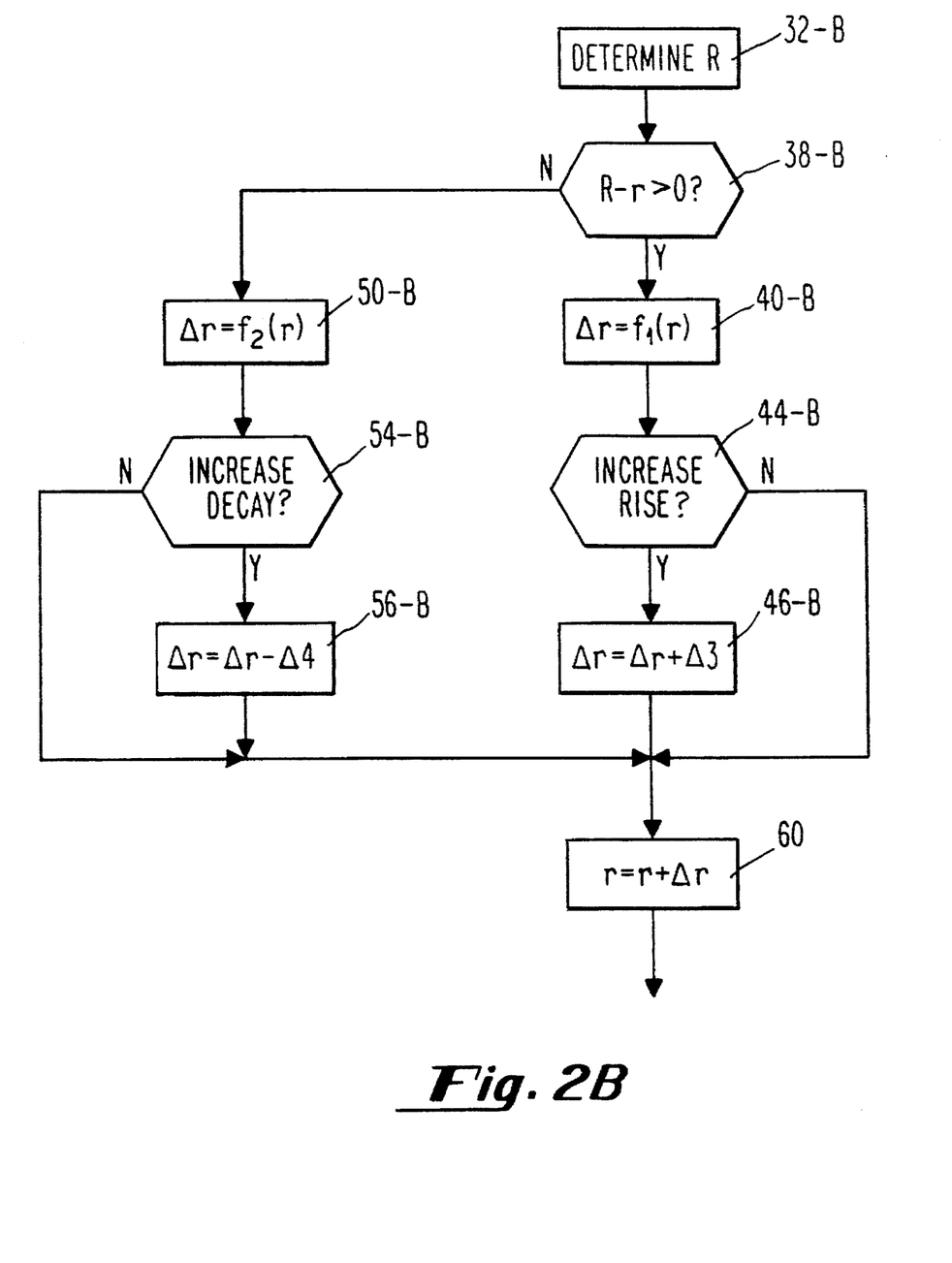

It is to be understood that FIG. 2A is reflective simply of logic steps taken to adjust the rise time or the decay time of the pacer response as a function of pacing rate and time rate of change of the sensor indicated rate. These steps may be combined with other logic decisions, such as consideration of total work done during exercise, as set forth in the above-mentioned application entitled "Work-Modulated Pacing Rate Deceleration." Further, rise time and/or decay time may be modulated as a function of a second sensor. Thus, if sensor rate r is determined primarily or solely from a first parameter such as Q-T interval, a second faster response sensor such as a typical activity sensor may be used to control rise time or decay time. For this embodiment, as seen in FIG. 2B, R is obtained from a first sensor, at 32-B. At 38-B it is determined whether rate should be incremented or decremented. If incremented, at 40-B $\Delta r$ is made equal to $f_1(r)$. Then, at 44B, the second sensor is monitored, to see if a faster response is indicated. If yes, $\Delta r$ is set equal to $\Delta r+\Delta 3$ at 46-B. If it is determined that rate should be decremented, at 50-B, $\Delta r$ is made equal to $f_2(r)$. Then, at 54-B, the second sensor signal is examined to determine whether a faster decay is indicated. If yes, at 56-B, $\Delta r$ is set equal to $\Delta r-\Delta 4$.

Referring now to FIG. 3, there is shown a block diagram of the major components of a pacemaker in accordance with this invention. Microprocessor circuitry 70 is illustrated, being comprised of microprocessor unit 70 and associated memory 72. The microprocessor itself may have built-in memory, in which case memory 72 is additional memory. The microprocessor circuitry is connected by data communication bus 73 to hardware block 75, and specifically to digital logic and control circuitry 76. This control circuitry is used for a number of conventional pacemaker operations, including controlling the timing, shape and size of output stimulus pulses. The digital logic and control circuitry 76 provides control signals to circuitry 81, which may generate a trial pace and/or ventricular pace pulses, which pulses are coupled on lead 83 to the atrium and/or the ventricle of the patient. Signals sensed from the heart are coupled through sense circuitry 82 back through to the logic and control circuitry 76. In addition, sensor 77 is shown, illustrated as an external sensor, which generates signals which are coupled through to amplifier and processing circuitry 78, and in turn coupled to circuitry 76 for developing of the R signal. Sensor 77 may be one or more external sensors, including a fast time-response sensor as discussed below, and may be co-utilized along with the Q-T signal, which latter signal is developed from the V sense circuitry in a known manner. Additionally, an external programmer 86 may be used which communicates with the pacemaker through transmit receive circuitry 87 in a standard fashion.

It is to be understood that variations of the disclosed preferred embodiments are within the scope of the invention. Thus, the invention may embody a combination of FIGS. 2A and 2B. In such a combination, rate increments can be determined to include either Δ1 and/or Δ3, and rate decrements can be determined to include either Δ2 and/or Δ4. In this way, changes can be determined as a function of pacing rate; time rate of change of the sensor-indicated pacing rate; and/or an extra sensor chosen to provide a fast time response. The contribution of the extra sensor in this arrangement is to accelerate the change of r so as to more quickly decrease the R-r difference.

Another embodiment of this invention involves controlling Δr as a function of the determined magnitude of the R-r value. Thus, instead of using one of the functions f1 or f2, as illustrated in FIG. 1B, Δr may be determined from a function f3, as illustrated in FIG. 4.

Figure 4:
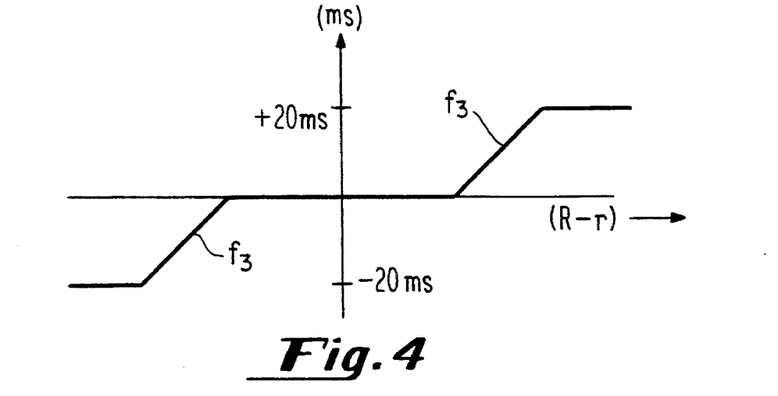
FIG. 4 is a graph indicating pacing rate increment versus the difference between sensor rate and current pacing rate (R-r).

In FIG. 4, Δr is zero until the magnitude of R-r exceeds a predetermined limit; Δr then increases linearly to a maximum value, such as 20 ms, and remains at such maximum value for even greater magnitudes (positive or negative values) of R-r. In this embodiment, steps 40 and 50 illustrated in FIG. 2A become "get Δr=f3 (R-r).

Figure 5:
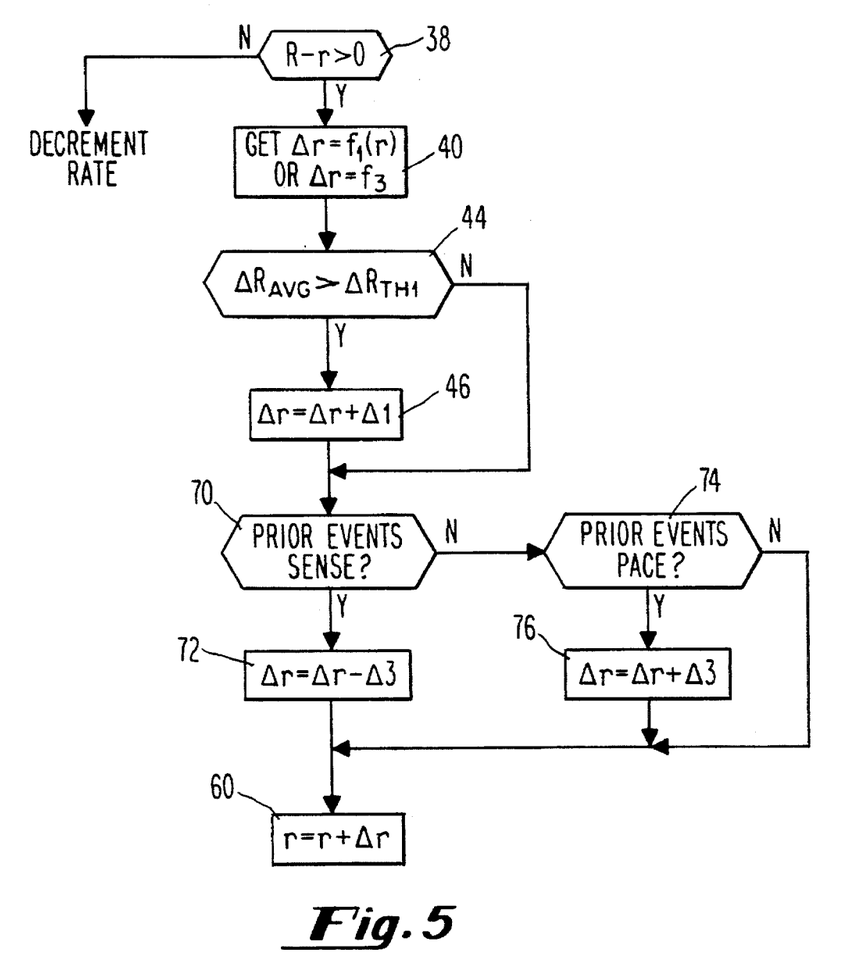
FIG. 5 is a flow diagram showing the primary logic steps for controlling pacing rate increment as a function of whether prior cycles have ended with sensed or paced events.

In yet another variation of this invention, the increment in pacing rate (Δr) can be modified depending upon whether the prior cycles were terminated with sensed natural beats, or paced beats. For example, the prior n cycles can be examined to determine if all resulted in sensed beats, or all resulted in paced beats. If sensed beats, the increase in Δr is limited, so that the sensor is not allowed to overtake the natural rate too quickly. If the prior n beats were paced, then the Δr increment can be made greater. This variation is illustrated in FIG. 5, which is a variation of FIG. 2A. As there illustrated, at 40, Δr is determined following a finding that R-r is positive, by using either the f1 or f3 function. Following blocks 44 and 46, at block 70 it is determined of the prior events have been sense events. If yes, Δr is decremented at 72; if no, the routine goes to 74, and determines whether the prior events have been paces. If yes, Δr is decremented by Δ3 at block 76.

What is claimed:

1. A rate responsive cardiac pacemaker, comprising a rate controllable pulse generator for generating stimulus pulses, sensor means for obtaining a sensor rate (R) which indicates desired pacing rate, and rate control means for developing a rate control signal for controlling said pulse generator to operate at a controlled pacing rate; and said rate control means further comprising:

first means for determining a difference between said sensor rate and said controlled pacing rate, second means for determining a measure of time rate of change of said sensor rate, and third means for adjusting said rate control signal as a function of said difference and said measure of time rate of change.

2. The pacemaker as described in claim 1, wherein said third means has increment means for adjusting said pacing rate by a calculated increment.

3. The pacemaker as described in claim 2, wherein said first means comprises means for determining whether said difference is positive or negative, and said third means determines said increment to be positive or negative corresponding to whether said difference is determined to be positive or negative.

4. The pacemaker as described in claim 3, wherein said third means comprises stored values of a rise threshold and a decay threshold, and rise comparison means for comparing said measure with said rise threshold when said difference is positive and decay comparison means for comparing said measure with said decay threshold when said difference is negative.

5. The pacemaker as described in claim 3, wherein said third means comprises first stored data representing a first correlation of said rate adjustment with said pacing rate for a determined positive rate difference, and second stored data representing a second correlation of said rate adjustment with pacing rate for a determined negative rate difference.

6. The pacemaker as described in claim 3, wherein said third means comprises first adjusting means for adjusting said increment by a first predetermined amount when said difference is positive and said measure exceeds a first threshold, and second adjusting means for adjusting said increment by a second amount when said difference is negative and said measure exceeds a second threshold.

7. The pacemaker as described in claim 1, wherein said first means comprises means for determining an average of said difference over a predetermined number of prior pacemaker cycles.

8. The pacemaker as described in claim 1, further comprising a fast response sensor means for indicating when rate adjustment can be accelerated, and wherein said third means comprises further means for further adjusting said rate control signal in response to an indication that rate adjustment can be accelerated.

9. A rate responsive cardiac pacemaker, comprising cyclical control means for controlling said pacemaker to operate cyclically with successive pacemaker cycles, a rate controllable pulse generator for generating stimulus pulses, sensor means for obtaining a sensor rate indication (R) which indicates desired pacing rate, and rate control means for developing a rate control signal each said pacemaker cycle for controlling said pulse generator to operate at a pacing rate, said rate control means having rate change means operative each cycle of said pacemaker for determining a measure of change of sensor rate, difference means operative each said pacemaker cycle for determining a difference between said sensor rate and said pacing rate, and said rate control means further comprising adjusting means operative each said pacemaker cycle for adjusting said pacing rate as a function of said measure of sensor rate change and said difference.

10. The pacemaker as described in claim 9, wherein said adjustment means comprises means operative each said pacemaker cycle for further determining whether prior pacemaker cycles have ended in sensed or paced events and means for adjusting said pacing rate as a function of said further determining.

11. A rate responsive pacemaker comprising a rate controllable pulse generator for generating stimulus pulses, sensor means for obtaining a sensor rate (R) which indicates desired pacing rate, and rate control means for developing a rate control signal for controlling said pulse generator at a controlled pacing rate (r), said rate control means further comprising:

(a) first means for determining a difference between said sensor rate and said controlled pacing rate and for determining when said difference is positive and when it is negative;

(b) rise means for determining an increment in pacing rate as a first function of pacing rate when said difference is positive and decay means for determining a first decrement in pacing rate as a second function of pacing rate when said difference is negative;

(c) rate means for determining a measure of time rate of change of said sensor rate; and (d) adjusting means for adjusting said rate control signal in accordance with said increment and said measure of said time rate of change when said difference is positive and in accordance with said decrement and said time rate of change when said difference is negative.

* * * * *

UNITED STATES PATENT AND TRADEMARK OFFICE
CERTIFICATE OF CORRECTION

PATENT NO. : 5,470,344
DATED : November 28, 1995
INVENTOR(S) : Malcolm J.S. Begemann It is certified that error appears in the above-indentified patent and that said Letters Patent is hereby corrected as shown below:

On the title page: Item [54] and Column 1, line 1, replace "PACEMAKE" with -- PACEMAKER --.

Signed and Sealed this

Thirteenth Day of February, 1996

Attest:

BRUCE LEHMAN

*Attesting Officer*     *Commissioner of Patents and Trademarks*